(12) United States Patent  
Nakao et al.

(10) Patent No.: US 8,815,803 B2
(45) Date of Patent: Aug. 26, 2014

(54) METHOD FOR INCREASING BODY HEIGHT COMPRISING SYSTEMIC ADMINISTRATION OF CNP-53

(75) Inventors: Kazuwa Nakao, Kyoto (JP); Akihiro Yasoda, Hyogo (JP); Hidetomo Kitamura, Shizuoka (JP)

(73) Assignee: Kazuwa Nakao, Kyoto-shi (JP)

( * ) Notice: Subject to any disclaimer, the term of this patent is extended or adjusted under 35 U.S.C. 154(b) by 730 days.

(21) Appl. No.: 10/594,763

(22) PCT Filed: Mar. 31, 2005

(86) PCT No.: PCT/JP2005/006837
§ 371 (c)(1),
(2), (4) Date: Sep. 29, 2006

(87) PCT Pub. No.: WO2005/094890
PCT Pub. Date: Oct. 13, 2005

(65) Prior Publication Data
US 2008/0312142 A1 Dec. 18, 2008

(30) Foreign Application Priority Data

Mar. 31, 2004 (JP) .................................. 2004-107871

(51) Int. Cl.
*A61K 38/22* (2006.01)
*A61P 19/08* (2006.01)
*C07K 14/475* (2006.01)

(52) U.S. Cl.
USPC ......... 514/12.4; 514/16.7; 514/17.1; 530/324

(58) Field of Classification Search
None
See application file for complete search history.

(56) References Cited

U.S. PATENT DOCUMENTS 6,034,231 A * 3/2000 Tanaka et al. .............. 536/23.51

FOREIGN PATENT DOCUMENTS

| JP | 2003-104908 A | 4/2003 |
| JP | 2003-113116 A | 4/2003 |
| WO | WO 02074234 A2 * | 9/2002 |

OTHER PUBLICATIONS

Schulz, 2005. Peptides. 26: 1024-1034).*
Komatsu et al, 2002. J Bone Miner Metab. 20: 331-336).*
Miyazawa et al (2002. Endincrinology. 143(9): 3604-3610).*
Yasoda et al (2008. Endocrinology. 150: 3138-3144).*
Newman et al (2003. Clin Genet. 63: 241-251).*
Buckley et al, 2000. Clinical Science. 99: 467-472.*
Li, Qin, "Protein CNP That Relates to Body Height Growing Is Found Out in Japan", Journal of Medical Intelligence, No. 1, p. 53, (2004).

(Continued)

*Primary Examiner* — Zachary Howard
(74) *Attorney, Agent, or Firm* — Birch, Stewart, Kolasch & Birch, LLP (57) ABSTRACT

This invention provides a composition for increasing a body height of a patient with short stature or an individual other than patients with short stature. More specifically, the invention provides: a composition for increasing the body height of an individual comprising a guanyl cyclase B (GC-B) activator as an active ingredient, the composition being to be administered to an individual free from FGFR3 abnormality; a method for increasing the body height of an individual free from FGFR3 abnormality which comprises activating GC-B; a method for screening an agent for increasing the body height of an individual which comprises selecting an agent for increasing the body height using GC-B activity as an indication; and a method for extending a cartilage bone free from FGFR3 abnormality which comprises activating GC-B in an individual.

5 Claims, 5 Drawing Sheets (56) References Cited

OTHER PUBLICATIONS

Tanaka, Kiyoshi, Natriuretic peptides as novel growth factor of growth plate cartilage, Clinical Calcium, 2002, vol. 12, No. 3, pp. 352 to 355.
Chusho, Hideki et al., Dwarfism and early death in mice lacking C-type natriuretic peptide, Proc.Nat.Acad.Sci.USA, 2001, vol. 98, No. 7, pp. 4016 to 4021.
Yasoda, Akihoro et al., Natriuretic peptide regulation of endochondral ossification, Evidence for possible reles of the C-type natriuretic peptide/guanylyl cyclase-B pathway, Journal of Biological Chemistry, 1998, vol. 273, No. 19, pp. 11695 to 11700.
Yasoda et al., "Overexpression of CNP in chondrocytes rescues achondroplasia through a MAPK-dependent pathway", Nature Medicine, vol. 10, No. 1, pp. 80-86, (Jan. 2004).
Kiemer et al., "Inhibition of Cyclooxygenase-2 by Natriuretic Peptides", Endocrinology, vol. 143, No. 3, pp. 846-852, (2002).
Johnson et al., "Distinct Transgutaminase 2-independent and Transglutaminase 2-dependent Pathways Mediate Articular Chondrocyte Hypertrophy", The Journal of Biological Chemistry, vol. 278, No. 21, pp. 18824-18832, (May 23, 2003).
Suda M et al: "Skeletal overgrowth in transgenic mice that overexpress brain natriuretic peptide." Proceedings of the National Academy of Sciences of the United States of America, Mar. 3, 1998, vol. 95, No. 5, pp. 2337-2342, XP-002541699.
Supplementary European Search Report dated Aug. 31, 2009 for corresponding EP-05728903.
JPO Office Action, Appl. No. 2006-511899, Jan. 25, 2011, pp. 1-3.
Yasoda, A. et al, "C-type natriuretic peptide (CNP)—a novel stimulator of bone growth formed through endochondral ossifcation," Nippon Rinsho, Feb. 28, 2004, vol. 62, suppl. 2, pp. 77-81.

\* cited by examiner

```
                        SEQUENCE LISTING

<160> NUMBER OF SEQ ID NOS: 10

<210> SEQ ID NO 1
<211> LENGTH: 22
<212> TYPE: PRT
<213> ORGANISM: Homo sapiens
<220> FEATURE:
<221> NAME/KEY: DISULFID
<222> LOCATION: (6)..(22)
<223> OTHER INFORMATION: A disulfide bond is formed

<400> SEQUENCE: 1

Gly Leu Ser Lys Gly Cys Phe Gly Leu Lys Leu Asp Arg Ile Gly Ser
 1               5                  10                  15

Met Ser Gly Leu Gly Cys
            20

<210> SEQ ID NO 2
<211> LENGTH: 53
<212> TYPE: PRT
<213> ORGANISM: Homo sapiens
<220> FEATURE:
<221> NAME/KEY: DISULFID
<222> LOCATION: (37)..(53)
<223> OTHER INFORMATION: A disulfide bond is formed

<400> SEQUENCE: 2

Asp Leu Arg Val Asp Thr Lys Ser Arg Ala Ala Trp Ala Arg Leu Leu
 1               5                  10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (6)..(22)
<223> OTHER INFORMATION: A disulfide bond is formed
```

```
<400> SEQUENCE: 3

Gly Leu Ser Lys Gly Cys Phe Gly Leu Lys Leu Asp Arg Ile Gly Ala
 1               5                  10                  15

Met Ser Gly Leu Gly Cys
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (6)..(22)
<223> OTHER INFORMATION: A disulfide bond is formed

<400> SEQUENCE: 4

Gly Leu Ser Lys Gly Cys Phe Gly Leu Lys Leu Asp Arg Ile Gly Ser
 1               5                  10                  15

Gln Ser Gly Leu Gly Cys
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (6)..(22)
<223> OTHER INFORMATION: A disulfide bond is formed

<400> SEQUENCE: 5

Gly Leu Ser Lys Gly Cys Phe Gly Leu Lys Leu Asp Arg Ile Gly Ser
 1               5                  10                  15

Ala Ser Gly Leu Gly Cys
            20

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(17)
<223> OTHER INFORMATION: A disulfide bond is formed

<400> SEQUENCE: 6

Cys Phe Gly Leu Lys Leu Asp Arg Ile Gly Ser Met Ser Gly Leu Gly
 1               5                  10                  15

Cys

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: DISULFID
<222> LOCATION: (7)..(23)
<223> OTHER INFORMATION: A disulfide bond is formed

<400> SEQUENCE: 7

Ser Leu Arg Arg Ser Ser Cys Phe Gly Leu Lys Leu Asp Arg Ile Gly
 1               5                  10                  15

Ser Met Ser Gly Leu Gly Cys
            20

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (6)..(22)
<223> OTHER INFORMATION: A disulfide bond is formed

<400> SEQUENCE: 8

Gly Leu Ser Lys Gly Cys Phe Gly Leu Lys Leu Asp Arg Ile Gly Ser
 1               5                  10                  15

Met Ser Gly Leu Gly Cys Asn Ser Phe Arg Tyr
            20                  25

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(17)
<223> OTHER INFORMATION: A disulfide bond is formed

<400> SEQUENCE: 9

Cys Phe Gly Leu Lys Leu Asp Arg Ile Gly Ser Gln Ser Gly Leu Gly
 1               5                  10                  15

Cys Asn Ser Phe Arg Tyr
            20

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MUTAGEN
<222> LOCATION: (4)..(4)
<223> OTHER INFORMATION: Xaa is Leu, Ile, or Val
<220> FEATURE:
<221> NAME/KEY: MUTAGEN
<222> LOCATION: (5)..(5)
<223> OTHER INFORMATION: Xaa is Lys, Leu, or Met
<220> FEATURE:
<221> NAME/KEY: MUTAGEN
<222> LOCATION: (6)..(6)
<223> OTHER INFORMATION: Xaa is Leu, Ile, Ala, or Val
<220> FEATURE:
<221> NAME/KEY: MUTAGEN
<222> LOCATION: (11)..(11)
<223> OTHER INFORMATION: Xaa is Ser, Ala, Gly, Thr, or Asn
<220> FEATURE:
```

```
<221> NAME/KEY: MUTAGEN
<222> LOCATION: (12)..(12)
<223> OTHER INFORMATION: Xaa is Met, Ala, Trp, His, Lys, Ser, or Gly
<220> FEATURE:
<221> NAME/KEY: MUTAGEN
<222> LOCATION: (12)..(12)
<223> OTHER INFORMATION: Xaa is Met, Ala, Trp, His, Lys, Ser, or Gly
<220> FEATURE:
<221> NAME/KEY: MUTAGEN
<222> LOCATION: (14)..(14)
<223> OTHER INFORMATION: Xaa is Gly, Lys, Ala, or Leu
<220> FEATURE:
<221> NAME/KEY: MUTAGEN
<222> LOCATION: (15)..(15)
<223> OTHER INFORMATION: Xaa is Leu or Met
<220> FEATURE:
<221> NAME/KEY: DISULFID
<222> LOCATION: (1)..(17)
<223> OTHER INFORMATION: A disulfide bond is formed

<400> SEQUENCE: 10

Cys Phe Gly Xaa Xaa Xaa Asp Arg Ile Gly Xaa Xaa Ser Xaa Xaa Gly
 1               5                  10                  15
Cys
```

METHOD FOR INCREASING BODY HEIGHT COMPRISING SYSTEMIC ADMINISTRATION OF CNP-53

The present application is a national stage application of PCT International Application PCT/JP2005/006837, filed Mar. 31, 2005.

TECHNICAL FIELD

The present invention relates to a composition for increasing the body height of an individual, comprising, a guanyl cyclase B (GC-B) activator as an active ingredient. More specifically, the composition of the present invention can be used for treatment of a patient with short stature free from FGFR3 abnormality, or for increasing the body height in an individual other than patients with short stature disease.

The present invention also relates to a method for increasing a body height of an individual by activation of GC-B.

The present invention further relates to a method for screening for an agent for increasing a body height of an individual using the activity of GC-B as an indication, and to a method for extending cartilage bones free from FGFR3 abnormality by the activation of GC-B.

BACKGROUND OF INVENTION

The term "short stature" is medically defined as height more than two standard deviation (−2SD) below the mean height of the population of individuals of the same sex and the same age. When this criterion is fulfilled with respect to an individual, such an individual is diagnosed as a short-statured syndrome or dwarfism. The short stature is roughly divided into: short stature caused by endocrine abnormalities such as hyposecretion of growth hormones or insulin-like growth factor-I (IGF-I); short stature caused by non-endocrine abnormalities, including familial short stature, fetal hypoplastic short stature, or chromosomal abnormality-caused short stature; and secondary short stature caused by chemotherapy or radiation therapy.

The short stature or dwarfism has been treated so far by administration of growth hormones or by orthopedic surgeries, such as replacement of a hip joint with an artificial joint or limb lengthening. In the case of limb lengthening, the bone is surgically cut at age 10 or older and the body height is gradually extended using a special machine (a limb lengthener) over a period of around half a year. This operation, however, imposes severe pain on the patient. In the case of growth hormone therapy, height growth can be improved via periodical injection of growth hormones from early childhood; however, growth would be terminated upon discontinuation of injection. Such treatment techniques are not intended to treat diseases, and are not considered to be ideal from the viewpoint of the quality of life (QOL) of patients (American Journal of Medical Genetics 1997, 72: 71-76; European Journal of Endocrinology 1998; 138: 275-280). The short stature caused by endocrine abnormalities is a disease capable of treating with drugs such as recombinant growth hormones or IGF-I. In contrast, the cause of a nonendocrine abnormality-caused short stature like familial short stature or fetal hypoplastic short stature has not yet been elucidated. Since the effect of growth hormones on nonendocrine abnormality-caused short stature has not been approved, there are no effective therapeutic agents against such short stature (the Merck Manual, 17$^{th}$ edition, 1999, Nikkei Business Publications, Inc./Nikkei BP Publishing Center, Inc., Japan). Under these circumstances, development of therapeutic agents based on new mechanisms has been demanded.

Guanyl cyclase (GC) is a membrane protein belonging to the enzyme family that catalyzes the synthesis of the second messenger cGMP from GTP, and its examples include GC-A, GC-B, . . . , and GC-F. GC-B is found mainly in vascular endothelial cells, and thought to be involved in relaxation of the smooth muscle.

Natriuretic peptides (NPs) are divided into ANP (atrial sodium peptide), BNP (brain natriuretic peptide) and CNP (type c natriuretic peptide), and they are thought to elevate an intracellular cGMP level through two guanyl cyclase conjugated receptors (NPR-A for ANP and BNP, and NPR-B for CNP) and to perform intracellular signal transduction mediated by a plurality of cGMP effecter molecules (Ann Rev Biochem 1991; 60: 229-255). NPs have been reported to play an important role in the control of humoral homeostasis and blood pressure (J Clin Invest 1987; 93:1911-1921, J Clin Invest 1994; 87: 1402-1412), and their expression and biological activity in various tissues other than the cardiovascular system are known (Endocrinol 1991; 129:1104-1106, Ann Rev Biochem 1991; 60: 553-575). Concerning cartilage bones, effectiveness of overexpression of BNP (Proc. Natl. Acad. Sci., U.S.A., 1998, 95: 2337-2342) or CNP in the joints on the treatment of achondrogenesis resulting from mutation of a fibroblast growth factor receptor 3 (FGFR3) gene has been reported (Nat. Med., 2004, 10 (1): 80-86; Japanese Patent Publication No. 2003-113116 A).

An object of the present invention is to provide a composition for increasing a body height of a patient with short stature or an individual other than patients with short stature, who is free from FGFR3 abnormality, for therapeutic, cosmetic, or other purposes.

It is another object of the present invention to provide a method for increasing a body height in a patient with short stature or an individual other than patients with short stature by the activation of GC-B, wherein said patient and individual are both free from FGFR3 abnormality.

A further object of the present invention is to provide a method for screening for an agent for increasing a body height using the activity of GC-B as an indication.

A still further object of the present invention is to provide a method for extending a cartilage bone free from FGFR3 abnormality by the activation of GC-B.

SUMMARY OF THE INVENTION

We have prepared a C-type natriuretic peptide (CNP) transgenic mouse, which expresses CNP, a guanyl cyclase B (GC-B) activator, systemically with elevated blood level of CNP, and then studied the effect of CNP on body height or on growth cartilage. As a result, we have now found that in the CNP transgenic mouse the increase in body height is accelerated, that the femoral growth plate cartilage becomes significantly thickened, and that, through the property analyses of such CNP transgenic mice, the increase in body height is accelerated by the effect of CNP on hematogenously in the absence of an abnormality in FGFR3.

Accordingly, the present invention comprises the following:

According to the first aspect, the present invention provides a composition for increasing a body height of an individual, comprising a GC-B activator as an active ingredient, the composition being to be administered to an individual free from FGFR3 abnormality.

In an embodiment of the invention, said composition is used for patients with short stature free from FGFR3 abnormality.

In another embodiment of the invention, said composition is used for individuals other than patients free from FGFR3 abnormality.

In another embodiment of the invention, said increase in body height is extension of cartilage bones.

In another embodiment of the invention, said increase in body height is extension of femora, tibiae, radiuses, and/or ulnae.

In another embodiment of the invention, said activator is a peptide.

In another embodiment of the invention, the peptide is CNP or a derivative thereof.

In another embodiment of the invention, the CNP is CNP-22 or CNP-53 from mammals, including human, or birds.

According to another embodiment of the present invention, the CNP is CNP-22 of SEQ ID NO: 1 or CNP-53 of SEQ ID NO: 2.

In another embodiment of the invention, said derivative has a deletion, substitution or addition of one or several amino acids in the amino acid sequence of SEQ ID NO: 1 or 2, while possessing a CNP activity.

According to the second aspect, the present invention provides a method for increasing a body height of an individual, comprising activating GC-B to increase the body height in an individual free from FGFR3 abnormality.

In an embodiment of the invention, said increase in body height is extension of cartilage bones.

In another embodiment of the invention, said increase in body height is extension of femora, tibiae, radiuses, and/or ulnae.

In another embodiment of the invention, the GC-B is activated by CNP or a derivative thereof.

In another embodiment of the invention, the CNP is CNP-22 or CNP-53 from mammals, including human, or birds.

In another embodiment of the invention, the CNP is CNP-22 of SEQ ID NO: 1 or CNP-53 of SEQ ID NO: 2.

In another embodiment of the invention, said derivative has a deletion, substitution or addition of one or several amino acids in the amino acid sequence of SEQ ID NO: 1 or 2, while possessing a CNP activity.

According to the third aspect, the present invention provides a method for screening of an agent for increasing the body height of an individual, comprising screening of candidate agents for an agent for increasing the body height using the activity of GC-B as an indication.

In an embodiment of the invention, the activity of GC-B is determined as an amount of produced intracellular cGMP.

In another embodiment of the invention, said method comprises, preparing a cultured cell line that has been forced to express GC-B, culturing the cell line in the presence or absence of a test substance, determining an amount of intracellular cGMP produced in the cell line, and screening candidate agents for an agent for increasing the body height of an individual using the difference, as an indication, in amounts of intracellular cGMP produced in the presence and absence of the test substance.

The present invention further provides a method for extending a cartilage bone free from FGFR3 abnormality in an individual comprising activating GC-B in the individual.

The specification of this application encompasses the contents as disclosed in the specification and/or drawings of Japanese Patent Application No. 2004-107871, which is claimed as a priority of the application.

BRIEF DESCRIPTION OF THE DRAWINGS

FIG. 1 shows the construction of a vector for preparing a CNP transgenic mouse.

FIG. 3 shows the results of a genotypical analysis of a CNP transgenic mouse. In the wild type mouse (WT) 3 signals (indicated as "Wild type CNP gene") were detected, while in the transgenic mouse (Tgm) 2 signals (indicated as "Transgene") derived from the transgene were detected in addition to the wild-type CNP gene.

FIG. 4 shows the growth curve of CNP transgenic mice on time. The naso-anal lengths of female CNP transgenic mice (TG) were significantly greater than those of a normal litter of female mice (WT) at 2 weeks old and thereafter (FIG. 4A). The naso-anal lengths of male CNP transgenic mice were significantly greater than those of a normal litter of male mice (WT) at 4 weeks old and thereafter (FIG. 4B). (*: $p<0.05$; **: $p<0.01$ vs. WT; unpaired Student's t-test)

FIG. 5 shows thickening of growth cartilage in femora of CNP transgenic mice. Each thickness of the resting layer, proliferating layer and hypertrophic layer, and the total thickness of these layers in the CNP transgenic mice (CNP Tgm) were significantly greater than those of the normal littermates (Wild type). (*: $p<0.05$; **: $p<0.01$ vs. Wild type; unpaired Student's t-test)

DETAILED DESCRIPTION OF THE INVENTION

The present invention is further described with reference to the figures.

Figure 3:
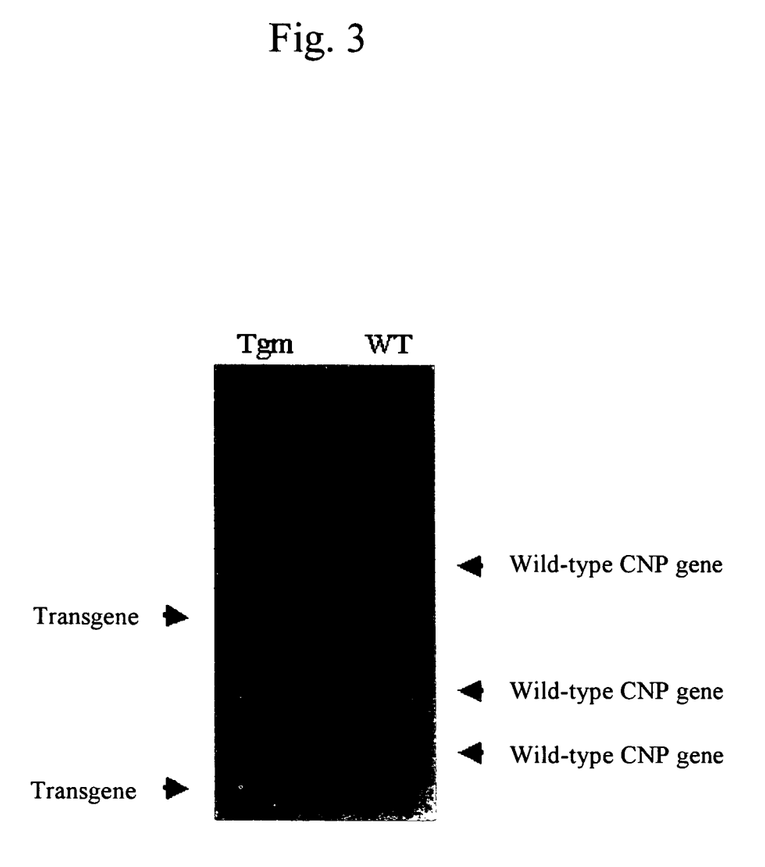

We analyzed the genotype of a CNP-transgenic mouse (CNP Tgm) produced as described later in Example 2 using Southern blotting. As a result, we detected 3 signals ("Wild type CNP gene") in the wild type mouse, while detecting 2 signals ("Transgene") derived from the transgene in the CNP Tgm in addition to the wild-type CNP gene, as shown in FIG. 3. The CNP levels in the liver, an organ expected to highly express said transgene, and in blood plasma were determined in order to study the expression of CNP in the CNP Tgm. As a result, it was found that the CNP Tgm showed about 10 fold and about 24 fold higher CNP levels in the liver and blood plasma, respectively, than the wild type, demonstrating statistically significant overexpression of CNP peptides (Table 1 in Example 4).

Figure 4A:
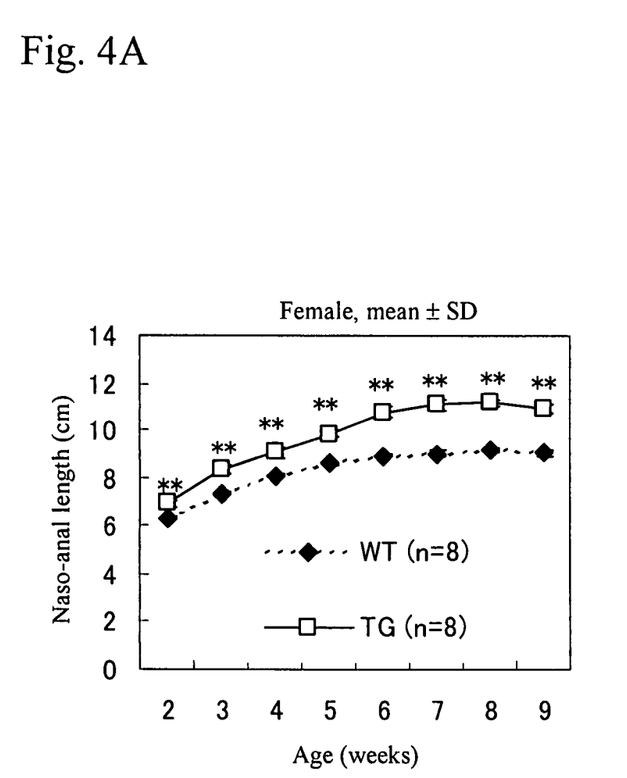
Figure 4B:
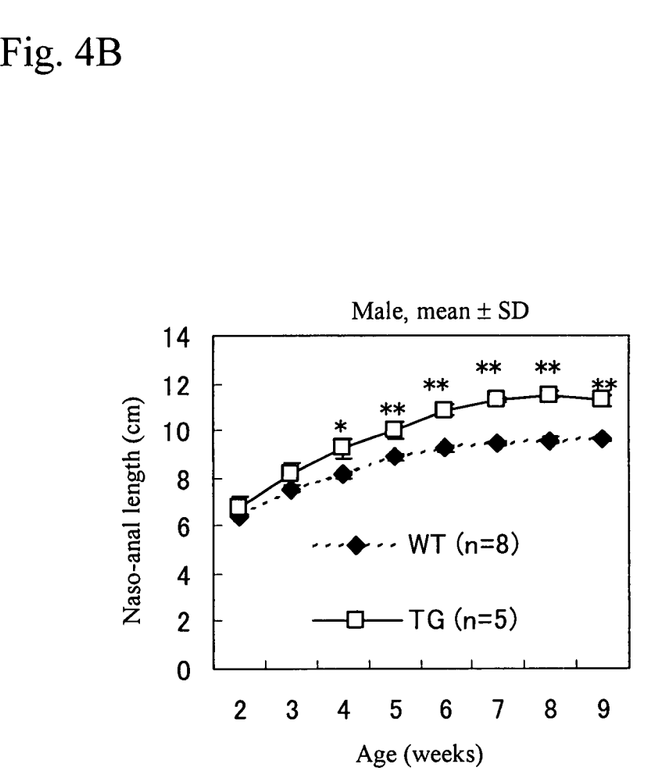

The naso-anal lengths of female and male CNP Tgms and normal litter were measured on time over a period of 2 to 9 weeks. As a result, the naso-anal lengths of the female and male CNP Tgms were greater than those of the normal litter, and the body heights of the CNP Tgms were more increased as well than the normal litter (FIG. 4A: female; FIG. 4B: male). Thus, it was confirmed that elevating a CNP level in blood resulted in acceleration of the increase in body height.

Figure 5:
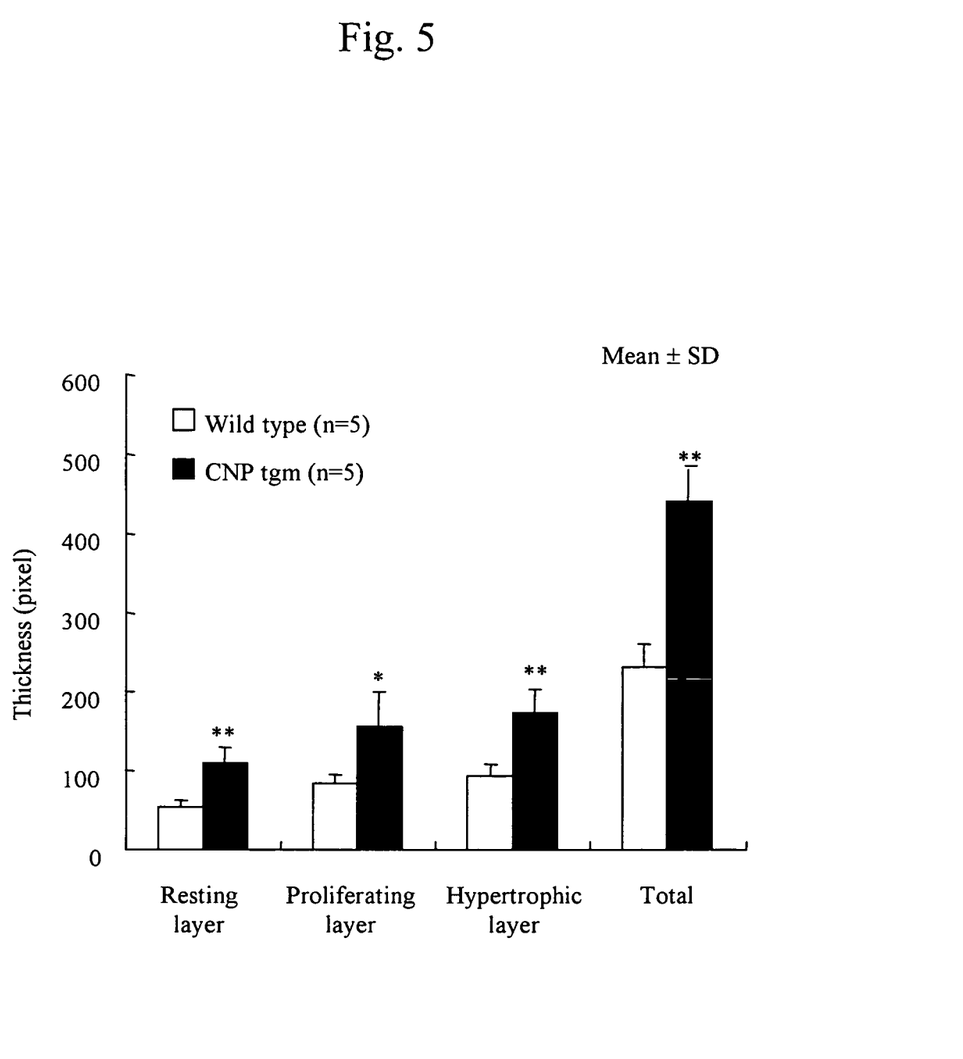

The thickness of the growth cartilage of CNP Tgm was histologically analyzed using the mean thickness of the resting layer, proliferating layer and hypertrophy layer of the growth cartilage on the patellar surface femur, and the total of the three layers (as the thickness of growth cartilage). As a result, it was confirmed that each thickness of the resting layer, proliferating layer and hypertrophy layer, and the total thickness thereof for CNP Tgm were greater with statistical significance than those of the wild type (FIG. 5). It was also demonstrated that CNP accelerates the increase in body height in animals by increasing each thickness of the resting layer, proliferating layers and hypertrophy layer of other cartilage bones, such as the tibiae, radiuses or ulnae, in addition to those of the cartilage bone of femora.

Thus, the present invention provides a composition for increasing a body height of an individual, comprising a GC-B activator as an active ingredient, the composition being to be administered to an individual free from FGFR3 abnormality.

In the present invention, the term "FGFR3 abnormality" refers to achondrogenesis or achondroplasia, which is caused by growth inhibition of cartilage bones resulting from mutations in the fibroblast growth factor receptor 3 (FGFR3) gene, or achondrogenesis or achondroplasia caused by function control failure of FGFR3 or overexpression of FGFR3 gene resulting from mutations in the FGFR3 gene (Japanese Patent Publication No. 2003-113116A; Nat. Med., 2004, 10(1): 80-86; and International Publication No. WO 02/074234).

According to an embodiment of the invention, the composition is used for a patient with short stature free from FGFR3 abnormality. In the present invention, the term "short stature" refers to any short statured symptom or dwarfism which is not caused by FGFR3 abnormality, including for example (1) short stature caused by endocrine abnormalities, such as short stature caused by growth hormone hyposecretion (pituitary dwarfism) or short stature caused by hypothyreosis or adrenocortical hyperfunction; (2) short stature caused by non-endocrine abnormalities, such as familial short stature, fetal hypoplastic short stature, or short stature caused by chromosome abnormalities (e.g., Turner's syndrome and Prader-Willi syndrome); and (3) secondary short stature caused by chemotherapy or radiation therapy.

According to another embodiment of the invention, the composition can be used for individuals free from FGFR3 abnormality other than patients with short stature. The present invention may be used for individuals free from FGFR3 abnormality other than patients with short stature, in the fields of cosmetics, medicine, and sports. Use for humans who have demands to increase their body heights is also within the scope of the invention.

Examples of the individuals who use of the present invention is intended include, but are not limited to, mammals including human, such as human, pig, and bovine. Preferred individual is a human.

According to another embodiment of the invention, the increase in body height is the extension of cartilage bones.

According to still another embodiment of the invention, the increase in body height is the extension of femora, tibiae, radiuses, and/or ulnae.

As used in the invention, the term "guanyl cyclase B (GC-B)" has the same meaning as natriuretic peptide receptor B (NPR-B).

As used in the invention, the term "activity of GC-B" has the same meaning as guanyl cyclase activity.

In the present invention, a guanyl cyclase B (GC-B) activator or GC-B activator is a peptide or a nonpeptidic low-molecular-weight compound, preferably a CNP peptide or a derivative thereof, that can bind to and activate GC-B, which is known as a CNP receptor. Peptides as used herein refer to a substance consisting of amide bond linkages of a plurality of (L-, D- and/or modified) amino acids, and include polypeptides and proteins. A GC-B activator can be identified, for example, by expressing a GC-B receptor in a cultured cell line such as COS-7, adding a candidate agent to the medium, culturing the cell line for a certain time period at a certain temperature (for example, 37° C., 5 minutes), and measuring the amount of intracellular cGMP produced (Science 1991, 252: 120-123). Using such an assay system, and using the amount of intracellular cGMP production as an indication, a GC-B activator may be identified and used in the present invention.

According to one embodiment of the invention, the GC-B activator is a peptide, and preferably CNP or a derivative thereof. Preferred CNP is selected from CNP-22 and CNP-53 from mammals, including human, or birds, and more preferably CNP-22 of SEQ ID NO: 1 or CNP-53 of SEQ ID NO: 2.

According to another embodiment of the invention, the CNP derivative as described above has a deletion, substitution or addition of one or several amino acids in the amino acid sequence of SEQ ID NO: 1 or SEQ ID NO: 2, while possessing a CNP activity. Alternatively, the CNP derivative comprises a sequence having about 70% or more, about 80% or more, about 85% or more, about 90% or more, about 95% or more, about 97% or more, about 98% or more, or about 99% or more identity with the amino acid sequence of SEQ ID NO: 1 or SEQ ID NO: 2 and retains CNP activity.

The term "one or several" as used herein generally represents any integer between 1 and 10, preferably between 1 and 5, more preferably between 1 and 3. The "% identity" between two amino acid sequences may be determined using techniques well known to those skilled in the art, such as BLAST protein search (Altschul, S. F., Gish, W., Miller, W., Myers, E. W. & Lipman, D. J. (1990) "Basic Local Alignment Search Tool" J. Mol. Biol. 215:403-410).

Examples of CNPs usable in the present invention include CNPs from mammals including human (CNP-22: Biochem. Biophys. Res. Commun. 1990; 168: 863-870, International Publication No. WO 91/16342, CNP-53: Biochem. Biophys. Res. Commun. 1990; 170:973-979, Japanese Patent Publication No. 4-74198A (1992), Japanese Patent Publication No. 4-139199A (1992), Japanese Patent Publication No. 4-121190A (1992)), CNPs from birds (Japanese Patent Publication No. 4-120094A (1992)), CNPs from amphibians (Japanese Patent Publication No. 4-120095A (1992)), and CNP derivatives such as CNP analogous peptides disclosed in Japanese Patent Publication No. 6-9688A (1994) and International Publication No. WO 02/074234.

CNP-22 and CNP-53, which consist of 22 and 53 amino residues respectively, are known as naturally occurring CNPs. Because CNPs have a high homology in their sequences between birds and mammals including human, i.e. regardless of the kind of animals, CNPs from birds and mammals including human, preferably CNPs from mammals including human, and more preferably CNPs from human, can be used in the present invention. The amino acid sequence of human CNP-22 or CNP-53 has the sequence shown in SEQ ID NO: 1 or SEQ ID NO: 2 respectively, represented by:

Gly Leu Ser Lys Gly Cys Phe Gly Leu Lys Leu Asp Arg Ile Gly Ser Met Ser Gly Leu Gly Cys (human CNP-22; SEQ ID NO: 1); or Asp Leu Arg Val Asp Thr Lys Ser Arg Ala Ala Trp Ala Arg Leu Leu Gln Glu His Pro Asn Ala Arg Lys Tyr Lys Gly Ala Asn Lys Lys Gly Leu Ser Lys Gly Cys Phe Gly Leu Lys Leu Asp Arg Ile Gly Ser Met Ser Gly Leu Gly Cys (human CNP-53; SEQ ID NO: 2), each of which has an intramolecular disulfide bond, i.e. between 6-Cys and 22-Cys in human CNP-22 or between 37-Cys and 53-Cys in human CNP-53, forming a cyclic peptide structure.

Pig CNP-22 and rat CNP-22 have the same amino acid sequence as human CNP-22, whereas the amino acid residues at positions 17 and 28 are His and Gly, respectively, in pig CNP-53 and rat CNP-53, and they are Gln and Ala in human CNP-53, i.e., two amino acids are different in CNP-53 between human and pig or rat (Japanese Patent Publication No. 4-139199A (1992), Japanese Patent Publication No. 4-121190A (1992), and Japanese Patent Publication No. 4-74198A (1992)). In addition, chicken CNP-22 has the same primary structure as human CNP-22, with the exception that the amino acid residue at position 9 is Val (Japanese Patent Publication No. 4-120094A (1992)).

The CNPs usable in the invention include CNPs purified from natural sources, recombinant CNPs produced by known genetic engineering techniques, and CNPs produced by known chemical syntheses (for example, a solid phase synthesis using peptide synthesizer), preferably human CNP-22 and human CNP-53 produced by genetic engineering techniques. Production of human CNPs by genetic engineering techniques comprises, for example, the steps of incorporating the DNA sequence of human CNP-22 or CNP-53 (Japanese Patent Publication No. 4-139199A (1992)) into a vector such as plasmid or phage, transforming the vector into a procaryotic or eucaryotic host cell, such as E. coli or yeast, and expressing the DNA in suitable culture medium, preferably allowing the cells to secrete the CNP peptide extracellularly, and collecting and purifying the CNP peptide produced. Polymerase chain reaction (PCR) technique can also be used to amplify target DNA.

Basic techniques such as genetic recombination, site-directed mutagenesis and PCR techniques are well-known to those skilled in the art, which are described, for example, in J. Sambrook et al., Molecular Cloning, A Laboratory Manual, Second Edition, Cold Spring Harbor Laboratory Press (1990); Ausubel et al., Current Protocols In Molecular Biology, John Wiley & Sons (1998), and said techniques as disclosed therein may be used for the present invention. As the vectors, commercially available vectors or vectors as disclosed in publications may also be used.

CNP derivatives that may be used in the present invention have the CNP activity and have a cyclic peptide structure having a disulfide bond between two cysteine residues as seen in human CNP-22 or CNP-53. Examples of the CNP derivatives include: fragments of the CNPs as described above; peptides having a substitution of at least one amino acid by another amino acid in the CNPs above or fragments thereof; peptides having a deletion of at least one amino acid in the CNPs above or partial peptides thereof; and peptides having an addition of at least one amino acid in the CNPs above or partial peptides thereof. As used herein, the substitution, deletion or addition of amino acids means that a certain number of amino acids are substituted, deleted or added by a well-known method such as site-directed mutagenesis, with the proviso that the CNP activity is not lost. For example, the CNP-22 or CNP-53 derivatives have a substitution, deletion or addition of one or several amino acids in the amino acid sequence of SEQ ID NO: 1 or SEQ ID NO: 2, possessing the CNP activity.

In general, the substitution of amino acids is preferably a substitution between conservative amino acids. Conservative amino acids may be classified according to, for example, polarity (or hydrophobicity) or types of electric charges. Examples of nonpolar, uncharged amino acids include glycine, alanine, valine, leucine, isoleucine, proline, etc.; aromatic amino acids include phenylalanine, tyrosine and tryptophan; polar, uncharged amino acids include serine, threonine, cysteine, methionine, asparagine, glutamine, etc.; negatively charged amino acids include aspartic acid and glutamic acid; and positively charged amino acids include lysine, arginine and histidine.

The term "CNP activity" as used herein refers to the activity to act on GC-B to increase guanyl cyclase activity or the activity to significantly increase the body height of an individual. The CNP activity can be determined by measuring cellular guanyl cyclase activity, for example by measuring the amount of intracellular cGMP produced, or alternatively by administering a GC-B activator for a certain period to an animal such as mouse or rat and subsequently measuring the naso-anal length as described in Example 5 later.

Examples of CNP-22 analogous peptides include the following cyclic peptides as described in Japanese Patent Publication No. 6-9688A (1994) and International Publication No. WO 02/074234, (wherein underlines represent variations from human CNP-22).

Gly Leu Ser Lys Gly Cys Phe Gly Leu Lys Leu Asp Arg Ile Gly Ala Met Ser Gly Leu Gly Cys (SEQ ID NO: 3)

Gly Leu Ser Lys Gly Cys Phe Gly Leu Lys Leu Asp Arg Ile Gly Ser Gln Ser Gly Leu Gly Cys (SEQ ID NO: 4)

Gly Leu Ser Lys Gly Cys Phe Gly Leu Lys Leu Asp Arg Ile Gly Ser Ala Ser Gly Leu Gly Cys (SEQ ID NO: 5)

Cys Phe Gly Leu Lys Leu Asp Arg Ile Gly Ser Met Ser Gly Leu Gly Cys (SEQ ID NO: 6)

SerLeuArgArgSerSer Cys Phe Gly Leu Lys Leu Asp Arg Ile Gly Ser Met Ser Gly Leu Gly Cys (SEQ ID NO: 7)

Gly Leu Ser Lys Gly Cys Phe Gly Leu Lys Leu Asp Arg Ile Gly Ser Met Ser Gly Leu Gly Cys AsnSerPheArgTyr (SEQ ID NO: 8)

Cys Phe Gly Leu Lys Leu Asp Arg Ile Gly Ser Gln Ser Gly Leu Gly Cys AsnSerPheArgTyr (SEQ ID NO: 9)

Cys Phe Gly Xaa Xbb XccAsp Arg Ile Gly Xdd Xee Ser Xff Xgg Gly Cys (wherein Xaa=Leu, Ile, Val; Xbb=Lys, Leu, Met; Xcc=Leu, Ile, Ala, Val; Xdd=Ser, Ala, Gly, Thr, Asn; Xee=Met, Ala, Trp, His, Lys, Ser, Gly; Xff=Gly, Lys, Ala, Leu; Xgg=Leu, Met) (SEQ ID NO: 10).

Examples of CNP-53 analogous peptides include cyclic peptides comprising amino acid variations similar to those of the CNP-22 analogous peptides.

The present invention also provides a method for increasing a body height in an individual, comprising activating GC-B to increase the body height in an individual free from FGFR3 abnormality. This invention is based on the finding that an GC-B activator can increase the body height of an individual free from FGFR3 abnormality. Specifically, the increase in body height is the extension of cartilage bones. More specifically, the increase in body height is the extension of femora, tibiae, radiuses, and/or ulnae. Specific examples of the GC-B activator are the CNPs or derivatives thereof as defined above. The CNP is preferably CNP-22 or CNP-53 from mammals, including human, or birds, and more preferably CNP-22 of SEQ ID NO: 1 or CNP-53 of SEQ ID NO: 2. The CNP derivatives have a substitution, deletion or addition of one or several amino acids in the amino acid sequence of SEQ ID NO: 1 or SEQ ID NO: 2, while possessing a CNP activity. Other GC-B activators can be identified, for example, by expressing a GC-B receptor in a cultured cell line such as COS-7, adding a candidate agent to the medium, culturing the cell line for a certain time period at a certain temperature (for example, 37° C., 5 minutes), and measuring the amount of intracellular cGMP produced (Science 1991, 252: 120-123). Thus, using such an assay system and using the amount of produced intracellular cGMP as an indication, a GC-B activator can be identified and used for the present invention.

The present invention further provides a method for screening an agent for increasing the body height of an individual, comprising screening candidate agents for an agent for increasing the body height using the activity of GC-B as an indication. According to an embodiment of this invention, the GC-B can be activated by the CNPs as defined above or derivatives thereof. Because the GC-B is known to catalyze the synthesis of the second messenger cGMP from GTP through guanyl cyclase activity, the GC-B activity can be determined as an amount of produced intracellular cGMP.

According to another embodiment of this invention, the method comprises preparing cultured cells that express GC-B or cells from articular chondrocytes, culturing the cells in the presence of a candidate agent, and screening candidate agents for an agent for increasing body heights using the activity of GC-B in the cells as an indication.

According to preferred embodiment of this invention, the method comprises preparing a cultured cell line that has been forced to express GC-B, culturing the cell line in the presence or absence of a test substance, determining an amount of intracellular cGMP produced in the cell line, and screening of candidate agents for an agent for increasing the body height of an individual using the difference, as an indication, in amounts of intracellular cGMP produced in the presence and absence of the test substance.

In the screening method of the present invention, it may comprise screening for an agent for increasing the body height by, for example, expressing a GC-B receptor in a cultured cell line such as COS-7, adding a candidate agent to the medium, culturing the cell line for a certain time period at a certain temperature (for example, 37° C., 5 minutes), and measuring the amount of intracellular cGMP produced (Science 1991, 252: 120-123).

Furthermore, the present invention provides a method for extending a cartilage bone free from FGFR3 abnormality in an individual, comprising activating GC-B in the individual. According to an embodiment of this invention, the extension of cartilage bones can be accelerated in vivo, ex vivo or in vitro through the activation of GC-B. According to a referred embodiment of the invention, the method comprises accelerating the extension of cartilage bones free from FGFR3 abnormality by adding a GC-B activator, when culturing bone or cartilage.

The composition of the present invention is formulated into preparations for oral or parenteral administration by combining the GC-B activator defined above as an active ingredient with a pharmaceutically acceptable carrier, excipient, additives, or the like.

The composition of the present invention comprises the GC-B activator defined above as an active ingredient, and further comprises a carrier, excipient, and other additives that are used in conventional manufactures of medicaments.

Examples of the carriers and excipients for preparation include lactose, magnesium stearate, starch, talc, gelatin, agar, pectin, gum arabic, olive oil, sesame oil, cacao butter, ethylene glycol, and others conventionally used.

Examples of solid compositions for oral administration include tablets, pills, capsules, powders, granules, and the like. In such solid compositions, at least one active ingredient is mixed with at least one inert diluent, such as lactose, mannitol, glucose, hydroxypropylcellulose, microcrystal cellulose, starch, polyvinylpyrrolidone, magnesium aluminometasilicate, or the like. The composition may, according to a conventional method, also contain additives other than inert diluents, for example, a lubricant such as magnesium stearate, a disintegrating agent such as fibrous calcium glycolate, and a dissolution auxiliary agent such as glutamic acid or aspartic acid. Tablets or pills may, as required, be coated with a glycocalyx, such as sucrose, gelatin or hydroxypropyl methylcellulose phthalate, or with a gastro- or enteric-film, or with two or more layers. Capsules of an absorbable material, such as gelatine, are also included.

Liquid compositions for oral administration may include pharmaceutically acceptable emulsions, solutions, suspensions, syrups and elixirs, and may also contain conventional inert diluents, such as purified water and ethanol. The composition may contain, other than the inert diluent, an adjuvant, such as wetting and suspending agents, a sweetening agent, a flavor, an aromatic, and a preservative.

Examples of parenteral injections include sterile aqueous or non-aqueous solutions, suspensions, and emulsions. Examples of aqueous solutions and suspensions include water for injection and physiological saline for injection. Examples of non-aqueous solutions and suspensions include propylene glycol, polyethylene glycol, vegetable oils such as olive oil, alcohols such as ethanol, and polysorbate 80®. These compositions may further contain adjuvants, such as preservatives, wetting agents, emulsifiers, dispersants, stabilizers (for example, lactose), and dissolution auxiliary agents (e.g., glutamic acid and aspartic acid). The above-described materials may be sterilized by conventional sterilization methods, such as filter sterilization with a microfiltration membrane, heat sterilization such as autoclaving, or incorporation of disinfectants. Injections may be liquid preparations, or freeze-dried preparations that may be reconstituted before use. Examples of excipients for freeze-drying include sugar alcohols and sugars, such as mannitol and glucose.

The therapeutic or prophylactic agent of the present invention is administered by either oral or parenteral administration methods commonly used for pharmaceuticals. Preferred are parenteral administration methods, for example, injection (e.g., subcutaneous, intravenous, intramuscular and intraperitoneal injections), percutaneous administration, trans-mucosal administration (e.g., transnasal and transrectal), and trans-pulmonary administration. Oral administration may also be used.

The dosage of a GC-B activator, preferably a CNP as defined above or a derivative thereof, which is an active ingredient contained in the composition of the present invention, may be determined depending on the type of disease to be treated, the severity of the disease, patient's age, and the like, and may generally range from 0.005 µg/kg to 100 mg/kg, preferably from 0.02 µg/kg to 5 mg/kg. However, the dosage of the pharmaceutical composition containing a CNP activator according to the present invention is not limited thereto.

The present invention includes, but is not limited to, the following.

(1) A composition for increasing a body height of an individual, comprising a guanyl cyclase B (GC-B) activator as an active ingredient, the composition being to be administered to an individual free from FGFR3 abnormality.

(2) The composition of (1) above, for use in a patient with short stature.

(3) The composition of (1) above, for use in an individual other than patients with short stature.

(4) The composition of (1) above, wherein the increase in body height is extension of cartilage bones.

(5) The composition of (1) above, wherein the increase in body height is extension of femora, tibiae, radiuses, and/or ulnae.

(6) The composition of (1) above, wherein the activator is a peptide.

(7) The composition of (6) above, wherein the peptide is C-type natriuretic peptide (CNP) or a derivative thereof (8) The composition of (7) above, wherein the CNP is CNP-22 or CNP-53 from mammals including human, or birds.

(9) The composition of (7) above, wherein the CNP is CNP-22 of SEQ ID NO: 1 or CNP-53 of SEQ ID NO: 2.

(10) The composition of (7) above, wherein the derivative has a deletion, substitution or addition of one or several amino acids in the amino acid sequence of SEQ ID NO: 1 or 2, while possessing a CNP activity.

(11) A method for increasing a body height of an individual, comprising activating GC-B to increase the body height in an individual free from FGFR3 abnormality.

(13) The method of (11) above, wherein the increase in body height is extension of femora, tibiae, radiuses, and/or ulnae.

(14) The method of (11) above, wherein the GC-B is activated by CNP or a derivative thereof (15) The method of (14) above, wherein the CNP is CNP-22 or CNP-53 from mammals, including human, or birds.

(16) The method of (14) above, wherein the CNP is CNP-22 of SEQ ID NO: 1 or CNP-53 of SEQ ID NO: 2.

(17) The method of (14) above, wherein the derivative has a deletion, substitution or addition of one or several amino acids in the amino acid sequence of SEQ ID NO: 1 or 2, while possessing a CNP activity.

(18) A method for screening an agent for increasing the body height of an individual, comprising screening candidate agents for an agent for increasing the body height using the activity of GC-B as an indication.

(19) The method of (18) above, which comprises preparing cultured cells that express GC-B or cells from articular chondrocytes, culturing the cells in the presence of a candidate agent, and screening candidate agents for an agent for increasing body heights using the activity of GC-B in the cells as an indication.

(20) The method of (18) above, wherein the activity of GC-B is determined as an amount of produced intracellular cGMP.

(21) The method of (18) above, wherein it comprises preparing a cultured cell line that has been forced to express GC-B, culturing the cell line in the presence or absence of a test substance, determining an amount of intracellular cGMP produced in the cell line, and screening candidate agents for an agent for increasing the body height of an individual using the difference, as an indication, in amounts of intracellular cGMP produced in the presence and absence of the test substance.

(22) A method for extending a cartilage bone free from FGFR3 abnormality in an individual, comprising activating GC-B in the individual.

The present invention will be described in more detail by the following examples, which are for illustrative purposes only and are not intended to limit the scope of the invention. Thus, the present invention is not limited to those examples.

EXAMPLES

Example 1

Construction of Vector for Preparing CNP Transgenic Mouse

Figure 1A:
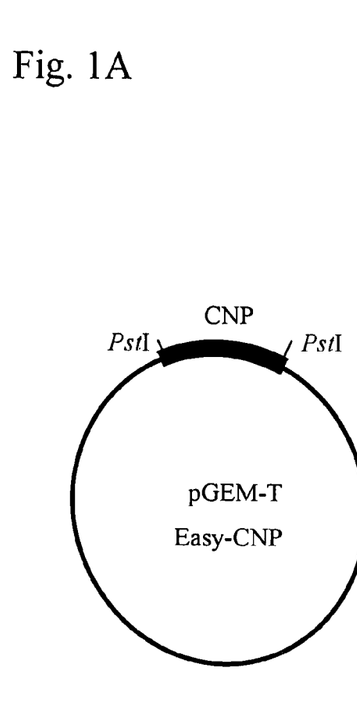
FIG. 1A: cDNA of the mouse CNP, which has been incorporated into pGEM-T Easy vector, was cut out with Pst I and blunt-ended at each end.
Figure 1B:
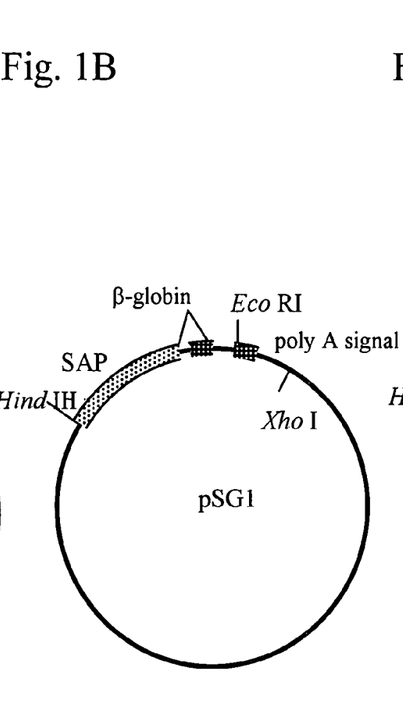
FIG. 1B: pSG1 was treated with EcoR I and blunt-ended.
Figure 1C:
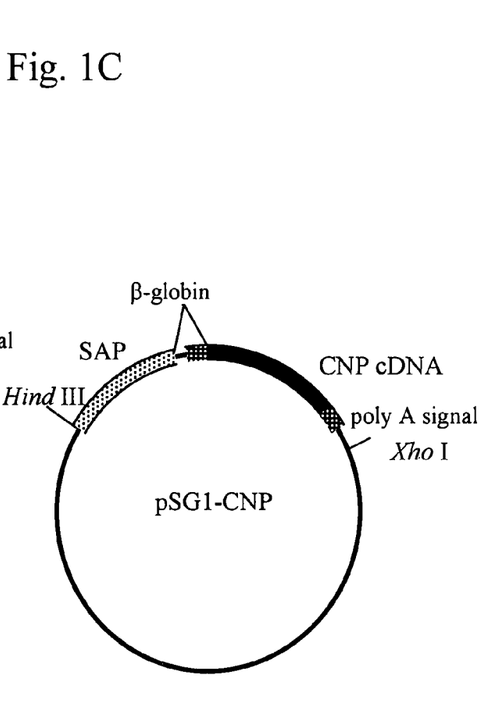
FIG. 1C: The mouse CNP cDNA prepared in FIG. 1A was incorporated into the pSG1 obtained in FIG. 1B.

As shown in FIG. 1A, the murine CNP cDNA (526 bp; FEBS Lett. 276:209-213, 1990) was subcloned into pGEM-T easy vector (Promega), and was then cut with Pst I and blunt-ended to prepare a mouse CNP cDNA. The vector PSG I (Promega; FIG. 1B) was cut with EcoRI, blunt-ended and ligated with the murine CNP cDNA, as shown in FIG. 1C, to prepare a SAP-mCNP vector (pSG1-CNP).

Example 2

Production of CNP Transgenic Mouse

Figure 2:
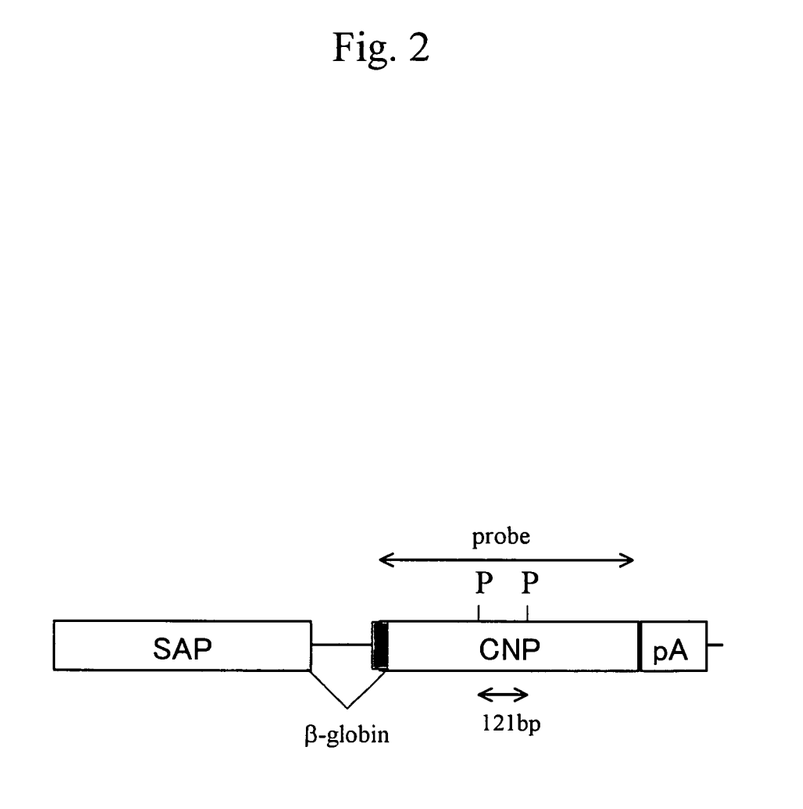
FIG. 2 shows a DNA fragment for injection. A fragment (about 2.3 kb) containing the CNP gene was cut out from pSG1-CNP prepared in FIG. 1C by digesting with Hind III and Xho I, and it was used as a fragment for injection.

A DNA fragment for injection was prepared as follows. The SAP-mCNP vector (pSG1-CNP; FIG. 1C) with an inserted CNP gene was first treated with Hind III and Xho I to cut out a fragment (about 2.3 kb) containing the CNP gene. The fragment was then collected using Gel Extraction Kit (QIAGEN), and was diluted with PBS⁻ at a concentration of 3 ng/μl, thereby obtaining the DNA fragment for injection (FIG. 2).

The mouse egg at pronucleus stage into which the DNA fragment was injected was collected as follows. First, a C57BL/6 female mouse (Clea Japan, Inc.) was injected intraperitoneally with 5 i.u pregnant mare serum gonadotropin (PMSG), and 48 hours later, with 5 i.u human chorionic gonadotropin (hCG), in order to induce superovulation. This female mouse was crossed with a congeneric male mouse. In the next morning of the crossing, in the female mouse the presence of a plug was confirmed and subsequently the oviduct was perfused to collect a mouse egg at pronucleus stage.

The DNA fragment for injection was injected into the pronucleus egg using a micromanipulator (Latest Technology in Gene Targeting (Yodosha, Japan), 190-207, 2000). Specifically, the DNA fragment was injected into 660 C57BL/6J embryos, and on the following day, 561 embryos at 2-cell stage were transplanted into the oviducts of recipient females on day 1 of false pregnancy at about 10 per each side of the oviduct (about 20/animal).

Recipient females, which had not been delivered of offsprings by the expected date of delivery, were subjected to cesarean section, resulting in the birth of offsprings which were raised by a foster mother. Total 136 offsprings were obtained, 5 of which were transgenic mice with an introduced CNP gene (hereafter referred to as "Tgm"). Hereinafter, the mouse initially obtained is referred to as the Founder.

All Founder mice were male, and the subsequent generation of offsprings (i.e., F1 mice) were obtained from four of the five lines.

Example 3

Genotype Analysis of CNP Transgenic Mouse

Genotype analysis was performed by Southern blotting according to procedures as described below.

The tail (about 15 mm) was taken from the 3-week old mouse and treated with proteinase K (at 55° C., with shaking at 100 rpm over day and night) to obtain a lysis solution. The obtained solution was then subjected to an automated nucleic acid separator (KURABO NA-1000; Kurabo, Japan) to prepare genomic DNA. The genomic DNA (15 μg) was treated with Pvu 11 (200 U), then with phenol-chloroform to remove the restriction enzyme, and was precipitated with ethanol to collect the DNA. The obtained DNA was dissolved in 25 μL of TE and subjected to electrophoresis on 0.7% agarose gel (at 50V constant voltage), then the gel was treated with 0.25M HCl solution for 15 minutes to cleave the DNA, washed with water, and blotted overnight onto a nylon membrane in 0.4M NaOH solution. Thereafter, the DNA on the membrane was fixed by the UV crosslink method. The membrane was treated (at 42° C. for 2 hours) with a hybridization solution (50% formamide, 0.5×Denhardt's, 0.5% SDS, 5×SSPE), and a $^{32}P$ labeled probe, which has been prepared with BcaBEST Labeling Kit (TaKaRa, Japan) using the CNP cDNA (about 0.5 kb) as a template, was added to the membrane for effecting hybridization at 42° C. overnight. After treatment with a detergent solution (2×SSC, 0.1% SDS) at 55° C. for 20 minutes, the membrane was exposed to Imaging Plate (Fuji Film) overnight to detect signals of the transgene using BAS2000 (Fuji Film, Japan) (FIG. 3). In the wild-type mouse (WT) 3 signals (wild-type CNP gene) were detected, while in the transgenic mouse (Tgm) 2 signals (transgene) derived from the transgene were detected in addition to the wild-type CNP gene.

Example 4

CNP Expression in CNP Transgenic Mouse

A CNP-22 EIA measuring kit (PHOENIX PHARMACEUTICALS INC.) was used for the determination of a CNP level.

Three each of 7-week old male and female CNP transgenic mice, as well as 3 each of male and female normal litter of mice, were euthanized by exsanguination from the postcava under ether anesthesia.

The liver, which is an organ expected to exhibit high expression of the transgene, was removed, and the EIA assay buffer from the measuring kit as above was added at 1 ml per 0.1 g of liver weight, followed by cooling on ice. The liver was homogenized in a Waring blender (Physcotron), and after centrifugation (at 2,000 rpm for 5 minutes), the supernatant was used as a sample for the determination of CNP-22 levels.

One mg of ethylenediaminetetraacetate-4Na (Junsei Chemical Co., Ltd., Japan) and 2 trypsin-inhibition units of aprotinin (Sigma) were added to the drawn blood and agitated to separate blood plasma, which was used as a sample for the determination of CNP-22 levels.

The results are shown in Table 1.

TABLE 1

CNP expression in CNP transgenic mouse

|  |  | Liver (ng/g tissue) | mean ± SD | Plasma (ng/mL) | mean ± SD |
|---|---|---|---|---|---|
| Wild type | No. 1 | 38.8 | 29.3 ± 20.5 | 0.3 | 0.3 ± 0.06 |
|  | No. 2 | 5.9 |  | 0.4 |  |
|  | No. 3 | 43.3 |  | 0.3 |  |
| CNP tgm | No. 1 | 293.3 | 290 ± 81.7** | 10.3 | 8.0 ± 4.7# |
|  | No. 2 | 370.0 |  | 11.1 |  |
|  | No. 3 | 206.7 |  | 2.6 |  |

**p < 0.01 (unpaired Student's t-test)

The CNP transgenic mouse showed about 10 fold and about 24 fold higher CNP-22 level in the liver and blood plasma respectively, than the wild type when the mean±SD values were compared between them. In each case the difference was statistically significant. It was confirmed, from the results, that the CNP peptide was overexpressed in the CNP transgenic mouse.

Example 5

Growth Curve of CNP Transgenic Mouse

The naso-anal lengths (in cm) of female and male CNP transgenic mice, as well as those of female and male normal littermates, were measured on time over a period of 2 to 9 weeks (FIG. 4). As a result, the naso-anal lengths of the female and male CNP transgenic mice were both greater than those of the normal littermates, demonstrating that the increase in body height has been accelerated. This also demonstrates that the increase of a CNP level in the blood results in the acceleration of increasing the body height.

Example 6

Histological Analysis of the Growth Cartilage of CNP Transgenic Mouse

For the purpose of analyzing the thickness of the growth cartilage histologically, 5 each of 9-week old female CNP transgenic mice and female normal litter of mice were euthanized by exsanguination from the postcava under ether anesthesia, and the thigh bone was fixed in 20% formalin for a week. After soaking in a 20% aqueous solution of EDTA-4Na (pH 7.4) (Junsei Chemical Co., Ltd., Japan) for decalcification, the patellar surface femur was subjected to a midline sagittal section and embedded in paraffin by conventional method to prepare a paraffin block. A 4 μm-thick section was further sectioned with a microtome to prepare paraffin sections, which were stained with hematoxylin and eosin. For the thickness of the growth cartilage, one microscopic field observed using an objective lens (×10) was incorporated into an image analysis software (IPAP, Sumika Technoservice, Japan), and each thickness of the resting layer, proliferating layer and hypertrophic layer was measured at 5 points in the microscopic field using the same software, and the calculated mean value thereof was taken as the thickness of each layer of the individual. The total of the three layers was regarded as the thickness of the growth cartilage of the individual. Mean values and standard deviations for these items were calculated between the CNP transgenic mice and the normal littermates (using Microsoft Excel 2000, Microsoft), and statistical analysis was performed using the unpaired Student's t-test (SAS ver. 6.12; SAS Institute Japan, Japan).

This statistical analysis revealed that, for each thickness of the resting layer, proliferating layer and hypertrophic layer, and the total thickness thereof in CNP transgenic mice (CNP Tgm), the thicknesses of the growth cartilage layers were greater with statistical significance than those of the normal mice (wild type) (FIG. 5). From the results, it was also demonstrated that the CNP, a GC-B activator, promotes the increase of the body height in mammals by increasing the thickness of each layer of growth cartilage.

INDUSTRIAL APPLICABILITY

The composition of the present invention, which comprises a GC-B activator as the active ingredient, enables the treatment of short statured symptoms, such as endocrine abnormality-caused short stature, non-endocrine abnormality-caused short stature, and secondary short stature, in an individual free from FGFR3 abnormality. The composition of the invention imposes less burden and pain on a patient, when compared with injection of growth hormones or insulin-like growth factor-I (IGF-I) or with orthopedic surgeries such as ostectomy. So, the composition can be an excellent therapeutic agent, which is beneficial for patient's QOL. It can also be used for increasing the body height in an individual free from FGFR3 abnormality and other than patients with short stature. Additionally, the present invention enables the extension of cartilage bones free from FGFR3 abnormality in vivo, ex vivo, or in vitro through the activation of GC-B.

All publications, patents, and patent applications cited herein are incorporated herein by reference in their entirety.

Free Text of Sequence Listing

Description in SEQ ID NO: 1: A disulfide bond is formed between 6-Cys and 22-Cys.

Description in SEQ ID NO: 2: A disulfide bond is formed between 37-Cys and 53-Cys.

Description of artificial sequence in SEQ ID NO: 3: CNP-22 derivative, where a disulfide bond is formed between 6-Cys and 22-Cys.

Description of artificial sequence in SEQ ID NO: 4: CNP-22 derivative, where a disulfide bond is formed between 6-Cys and 22-Cys.

Description of artificial sequence in SEQ ID NO: 5: CNP-22 derivative, where a disulfide bond is formed between 6-Cys and 22-Cys.

Description of artificial sequence in SEQ ID NO: 6: CNP-22 derivative, where a disulfide bond is formed between 1-Cys and 17-Cys.

Description of artificial sequence in SEQ ID NO: 7: CNP-22 derivative, where a disulfide bond is formed between 7-Cys and 23-Cys.

Description of artificial sequence in SEQ ID NO: 8: CNP-22 derivative, where a disulfide bond is formed between 6-Cys and 22-Cys.

Description of artificial sequence in SEQ ID NO: 9: CNP-22 derivative, where a disulfide bond is formed between 1-Cys and 17-Cys.

Description of artificial sequence in SEQ ID NO: 10: CNP-22 derivative, where 4-Xaa=Leu, Ile, Val; 5-Xaa=Lys, Leu, Met; 6-Xaa=Leu, Ile, Ala, Val; 11-Xaa=Ser, Ala, Gly, Thr, Asn; 12-Xaa=Met, Ala, Trp, His, Lys, Ser, Gly; 14-Xaa=Gly, Lys, Ala, Leu; 15-Xaa=Leu, Met and where a disulfide bond is formed between 1-Cys and 17-Cys.

What is claimed is:

1. A method for increasing the body height of an individual free from fibroblast growth factor receptor 3 (FGFR3) abnormality, comprising administering systemically C-type natriuretic peptide (CNP) or a derivative thereof to increase the body height in the individual,
    wherein the individual has growth cartilage layers,
    wherein the CNP is CNP-53 of SEQ ID NO: 2,
    wherein the derivative is selected from the group consisting of: CNP derivatives which are obtained from the amino acid sequence of SEQ ID NO: 2 by replacing all of residues 32-53 of SEQ ID NO:2 with a sequence selected from the group consisting of the amino acid sequences of SEQ ID NOs: 3 to 10, wherein the CNP derivatives possess a CNP activity.

2. The method of claim 1, wherein the increase in body height is extension of cartilage bones.

3. The method of claim 1, wherein the increase in body height is extension of femora, tibiae, radiuses, or ulnae.

4. The method of claim 1, wherein the CNP or the derivative thereof is CNP-53 of SEQ ID NO:2.

5. A method for extending a cartilage bone free from FGFR3 abnormality in an individual, comprising administering systemically C-type natriuretic peptide (CNP) or a derivative thereof to activate guanyl cyclase B (GC-B) in the individual,
    wherein the individual has growth cartilage layers,
    wherein the CNP is CNP-53 of SEQ ID NO: 2,
    wherein the derivative is selected from the group consisting of: CNP derivatives which are obtained from the amino acid sequence of SEQ ID NO: 2 by replacing all of residues 32-53 of SEQ ID NO:2 with a sequence selected from the group consisting of the amino acid sequences of SEQ ID NOs: 3 to 10, wherein the CNP derivatives possess a CNP activity.

* * * * *